United States Patent [19]

Karaki et al.

[11] Patent Number: 4,920,803
[45] Date of Patent: May 1, 1990

[54] ULTRASONIC MICROSCOPE APPARATUS

[75] Inventors: Kouichi Karaki, Hino; Mitsugu Sakai; Yasuo Sasaki, both of Hachioji, all of Japan

[73] Assignee: Olympus Optical Co., Ltd., Japan

[21] Appl. No.: 235,544

[22] Filed: Aug. 24, 1988

[51] Int. Cl.$^5$ ............................................. G01N 29/00
[52] U.S. Cl. ..................................................... 73/606
[58] Field of Search ................ 73/606, 607, 619, 620, 73/644

[56] References Cited

U.S. PATENT DOCUMENTS 4,378,699  4/1983  Wickramasinghe ................... 73/606
4,567,767  2/1986  Quate et al. ............................ 73/606

FOREIGN PATENT DOCUMENTS 62-231159  10/1987  Japan ..................................... 73/606

OTHER PUBLICATIONS

Review of Progress & Applications in Acoustic Microscopy; by L. W. Kessler, Journal Acoustic Soc. Am., vol. 55, No. 5, May 1974.

Primary Examiner—Jerry W. Myracle
Assistant Examiner—Louis M. Arana
Attorney, Agent, or Firm—Arnold, White & Durkee

[57] ABSTRACT

An ultrasonic microscope apparatus using cryogenic fluid as an ultarsonic propagating medium including a top loading space, in which specimen can be exchanged as the space kept airtight, and x-, y- and z-direction adjusting devices by means of which the relative position and the distance between the specimen and an acoustic lens can be adjusted under an airtight condition. The ultrasonic microscope apparatus also includes a vapor pressure adjusting device for adjusting the vapor pressure within a heat insulated vessel, in which the cryogenic fluid is contained, to prevent the cryogenic fluid from boiling.

47 Claims, 5 Drawing Sheets

ULTRASONIC MICROSCOPE APPARATUS

BACKGROUND OF THE INVENTION

Field of the Invention and Related Art Statement

The present invention relates to an ultrasonic microscope apparatus, particularly to an ultrasonic microscope apparatus using cryogenic fluids, such as liquid nitrogen, liquid argon and liquid helium, as an ultrasonic propagating medium.

Heretofore, there has been utilized an ultrasonic microscope apparatus in which a specimen to be observed is scanned in two-dimensional directions by an ultrasonic beam and an acoustic image of the specimen is obtained by receiving the ultrasonic wave reflected from the specimen or transmitted through the specimen. In the ultrasonic microscope apparatus mentioned above, it has been necessary to improve the resolving power for the image of the specimen in order to obtain more accurate image data from the specimen.

The plane resolving power of ultrasonic microscope apparatus depends on the wavelength of the acoustic wave propagating through the ultrasonic propagating medium. There is a relation of $c = f \cdot \lambda$, among the velocity c, the frequency f and the wavelength $\lambda$ of an acoustic wave in the medium. Therefore, in order to improve the resolving power, i.e. in order to make the wavelength of the acoustic wave shorter, one can either to make the frequency of the acoustic wave higher or use an ultrasonic propagating medium having a lower velocity of sound. Since water is used as an ultrasonic propagating medium in the known ultrasonic microscope apparatus, the resolving power has been improved by former means, i.e. making the frequency of the acoustic wave higher. However, in practice, there is a limitation in making the frequency higher, because the amount of absorption of the acoustic wave propagating through the ultrasonic propagating medium is proportional to the square of the frequency f of acoustic wave. That is to say, in order to obtain a large enough S/N for the image of a specimen, it is necessary to receive reflected waves having an intensity higher than a predetermined level. Therefore, in making the frequency of acoustic wave higher, it is necessary to shorten the distance over which the acoustic wave propagates in the ultrasonic propagating medium, so that the intensity of reflected wave is not decreased by the absorption. This means that the so-called working distance of an acoustic lens used in the ultrasonic microscope apparatus should be small, in other words, the radius of curvature of the acoustic lens has to be small.

In the ultrasonic microscope apparatus being utilized today, a resolving power of $0.7 \sim 0.5$ $\mu$m is obtained under the frequency of 1.5 GHz $\sim$ 2.0 GHz. Such resolving power corresponds to the circumstance where a specimen is observed by a general optical microscope in which the radius of curvature of the objective is about 50 $\mu$m $\sim$ 30 $\mu$m and its working distance is about 30 $\mu$m $\sim$ 10 $\mu$m. In order to obtain the more qualified resolving power in the ultrasonic microscope apparatus, it is necessary to make the working distance of the acoustic lens smaller. However, this requirement could not be satisfied due to the difficulties in manufacturing the acoustic lens and in using the apparatus.

As described above, the resolving power of ultrasonic microscopes using water as the ultrasonic propagating medium has now become substantially identical with that of optical microscopes. However, a more improved resolving power, which is higher than that of the optical microscope, is required for ultrasonic microscopes when observing electronic devices, for example, very large scale integration elements or ceramic elements. Then, it is necessary to develop a ultrasonic microscope apparatus having a higher resolving power.

In order to increase the resolving power development of an ultrasonic microscope apparatus using cryogenic fluid, for example, liquid nitrogen, liquid argon or liquid helium, as an ultrasonic propagating medium, in which the acoustic velocity c and the absorption amount of the acoustic wave are smaller than those of water has been considered. Such an ultrasonic microscope apparatus using cryogenic fluid as the propagating medium is mentioned in the Journal of Acoustic Society of America, vol. 67 (1980) pp. 1629 $\sim$ 1637. This known ultrasonic microscope apparatus comprises a heat insulated vessel, a stand for specimen arranged at the bottom of the heat insulated vessel, and an acoustic lens which is arranged above the stand, so that the specimen is scanned in two dimensions. Since this known ultrasonic microscope apparatus was developed only for the purpose of recognizing experimentally that its resolving power is much better than that of the apparatus using water, it has some drawbacks when putting it to practical use as described in the following.

The first drawback is that the field of view becomes small because the field of view is limited to about 40 $\mu$m $\times$ 30 $\mu$m in order to obtain the desired resolving power. Hence it is difficult to adjust the position of the specimen to be observed into the field of view. For instance, in the case of testing an IC to find defects thereof by using the ultrasonic microscope apparatus, a field of view having the dimension of at least 1 mm $\times$ 1 mm is necessary to adjust the position of IC for practical use. Therefore, the adjustment of the specimen's position is difficult in the known ultrasonic microscope apparatus.

The second drawback is that the operation for exchanging specimens is troublesome. When mounting a specimen after the observation for one specimen is concluded, it is necessary to take off the cap of the heat insulated vessel and remove the stand on which the acoustic lens, the supporting member therefor and the specimen are arranged, to the outside of the vessel. In this case, when the acoustic lens and the supporting member therefor are taken out of the cryogenic fluid to the outside, the moisture of outside air will freeze on the surfaces of these members in a moment and these members could not be used again. Also, when the cap of heat insulated vessel is removed, the moisture of the outside air enters into the vessel. Then the entered moisture might adhere onto the surface of the acoustic lens and specimen and thus forming a layer of water or ice thereon, so that it will be difficult to observe the specimen exactly. Further, when the next specimen is mounted into the heat insulated vessel, the specimen is cooled. Therefore, the moisture of the outside air that entered into the vessel will freeze on the surface of the specimen and thus it is impossible to observe exactly the specimen.

Moreover, in order to obtain an ultrasonic image having a high resolving power, it is necessary to adjust the ultrasonic beam exactly focused by the acoustic lens to the specimen. For this purpose, it is necessary to adjust the distance between the acoustic lens and the specimen from the outside under conditions where the heat insulated vessel including the acoustic lens and specimen therein is tightly closed.

And furthermore, cryogenic fluid such as liquid nitrogen, liquid argon, and liquid helium is boils under normal atmospheric pressure, and it is necessary to observe the specimen without the fluid boiling. If the cryogenic fluid is boiling when observing a specimen, the acoustic lens and the specimen are vibrated so that a clear ultrasonic image can not be obtained. In this case, boiling may be avoided if the heat insulated vessel containing the cryogenic fluid is closed up tight while observing and the vapor pressure of the space in contact with the surface of the cryogenic fluid is made higher than the normal atmospheric pressure, because the boiling point of a cryogenic fluid depends on vapor pressure.

However, if observation is continued with the vessel closed up tight, the vapor pressure of the space in contact with the surface of the cryogenic fluid will continue to increase, because the cryogenic fluid continues to evaporate according to the inflow of heat from the outside. The supporting member for the sample rod of the apparatus will be deviated thereby, and thus the position of the sample rod will be also deviated, so that adjustment of the focus of the acoustic lens to the specimen cannot be achieved. And, there is a danger that all sorts of members of the apparatus might explode by increasing the vapor pressure inside the vessel.

SUMMARY OF THE INVENTION

The object of the present invention is to solve the many kinds of drawbacks mentioned above and to provide an ultrasonic microscope apparatus in which an ultrasonic image having a high resolving power can be observed.

According to the first aspect of the invention, an ultrasonic microscope apparatus comprises:

a heat insulated vessel having an opening at the upper portion thereof for containing a cryogenic fluid serving as an ultrasonic propagating medium;

a sample rod having one end on which a specimen to be observed is supported, said sample rod being introduced into and withdrawn from said heat insulated vessel via said opening such that the specimen is immersed in the cryogenic fluid contained in the vessel;

an acoustic lens arranged in said heat insulated vessel such that the acoustic lens is immersed in the cryogenic liquid, for making an ultrasonic beam incident upon said specimen, when the sample rod is inserted into said heat insulated vessel;

scanning means for driving said acoustic lens in two-dimensional directions relative to the specimen;

a sliding seal member adapted to selectively take a first operational mode in which it moves integrally with said sample rod, and a second operational mode in which the sample rod moves slidably relative to said sliding sleeve member; and a hollow airtight member arranged to be transformable, one end of which is airtightly connected to said sliding seal member and the other end of which is airtightly connected to said heat insulated vessel.

In the ultrasonic microscope apparatus mentioned above, the slide seal member connected to the sample rod and the transformable hollow closure member form a transformable airtight top loading space, which is connected to the space formed in the heat insulated vessel. As a result, all sorts of operations for the sample rod, for example, making the sample rod to move in all directions, can be conducted under a closed up condition by using the transformable top loading airspace.

Further, according to the second aspect of the invention, an ultrasonic microscope apparatus comprises:

a heat insulated vessel having an opening at the upper portion thereof for containing a cryogenic fluid serving as an ultrasonic propagating medium;

a sample rod having one end on which a specimen to be observed is supported, said sample rod being introduced into and withdrawn from said heat insulated vessel via said opening such that the specimen is immersed in said cryogenic fluid;

an acoustic lens arranged in said heat insulated vessel such that the acoustic lens is immersed in the cryogenic fluid for making an ultrasonic beam incident upon said specimen;

scanning means for driving said acoustic lens in two-dimensional directions relative to the specimen;

a sliding seal member adapted to selectively take a first operational mode in which it moves integrally with the sample rod and a second operational mode in which the sample rod moves slidably relative to the sliding member;

a hollow airtight member arranged to be transformable and having one end connected to said sliding seal member, said hollow airtight member forming together with said sliding seal member a top loading space;

valve means arranged between the other end of said hollow airtight member and said opening of the the insulated vessel, for selectively communicating said top loading space and the heat insulated vessel with each other; and exhausting means for exhausting said top loading space.

In the apparatus mentioned above, the connecting condition between the top loading space and the space formed in the heat insulated vessel is controlled by the valve means. Therefore, the heat insulated vessel can be always kept airtight when the specimen which has been observed is exchanged by a next specimen, because the next specimen is first kept in the vacuum space of the top loading space and then is inserted into the cryogenic fluid contained in the heat insulated vessel. Thus, the apparatus prevents the moisture of the outside from entering into the vessel.

Further, according to the third aspect of the invention, an ultrasonic microscope apparatus comprises:

a heat insulated vessel having an opening at the upper portion thereof for containing a cryogenic fluid serving as an ultrasonic propagating medium;

a sample rod having one end on which a specimen to be observed is supported, said sample rod being introduced into and withdrawn from said heat insulated vessel via said opening such that the specimen is immersed in the cryogenic fluid contained in the vessel;

an acoustic lens arranged in said heat insulated vessel such that the acoustic lens is immersed in the cryogenic fluid for making an ultrasonic beam incident upon said specimen when the sample rod is inserted into said heat insulated vessel;

scanning means for driving said acoustic lens in two-dimensional directions relative to the specimen;

a supporting device for supporting said sample rod airtightly;

x-direction adjusting means for adjusting said sample rod in an x-direction which is perpendicularly to the ultrasonic incident direction;

y-direction adjusting means for adjusting said sample rod in a y-direction which perpendicular to the ultrasonic incident direction and said x-direction; and a hollow airtight member being transformable in said x- and y-directions, one end of which is airtightly connected to said supporting member and the other end of which is airtightly connected to said heat insulated vessel.

In the apparatus just mentioned above, the sample rod can be moved freely into the x- and y-directions under the airtight condition, and therefore it is possible to dispatch the ultrasonic beam toward the desired part of the specimen. As a result, it is possible to adjust the position of the specimen such that any desired part of specimen can be brought within the field of view of the acoustic lens from the external under the airtight condition.

Further, according to the fourth aspect of the invention, an ultrasonic microscope apparatus comprises:

a heat insulated vessel having an opening at the upper portion thereof for containing a cryogenic fluid serving as an ultrasonic propagating medium;

a sample rod having one end on which a specimen to be observed is supported, said sample rod being introduced into and withdrawn from said heat insulated vessel via said opening such that the specimen is immersed in the cryogenic fluid;

an acoustic lens arranged in said heat insulated vessel such that the acoustic lens is immersed in the cryogenic fluid for making an ultrasonic beam incident upon said specimen;

scanning means for driving said acoustic lens in two dimensional directions relative to the specimen;

supporting means for supporting said sample rod in an airtight manner;

z-direction ultrafine adjusting means for adjusting said sample rod in the ultrasonic incident direction; and a hollow airtight member being transformable into the ultrasonic incident direction, one end of which is airtightly connected to said supporting member and the other end of which is airtightly connected to said heat insulated vessel.

In the apparatus mentioned above, since the z-direction ultrafine adjusting means is connected to the sample rod supporting means, it is possible to finely adjust the distance between the specimen and the acoustic lens under the airtight condition. As a result, the ultrasonic beam emitted from the acoustic lens is focused on the specimen precisely by external controlling, and thus a ultrasonic image having a high resolving power can be obtained.

Furthermore, according to the fifth aspect of the invention, an ultrasonic microscope apparatus comprises;

a heat insulated vessel having an opening at the upper portion thereof for containing a cryogenic fluid serving as an ultrasonic propagating medium;

a sample rod having one end on which a specimen to be observed is supported, said sample rod being introduced into and withdrawn from said heat insulated vessel via said opening such that the specimen is immersed in said cryogenic fluid;

an acoustic lens arranged in said heat insulated vessel such that the acoustic lens is immersed in the cryogenic fluid for making an ultrasonic beam incident upon said specimen;

scanning means for driving said acoustic lens in two-dimensional directions relative to the specimen;

supporting means for supporting said sample rod airtightly;

inclination adjusting means connected to said supporting means for adjusting the inclination of the sample rod in mutually orthogonal x- and y-directions which are perpendicular to an ultrasonic incident direction; and a hollow airtight member being transformable in said x and y directions, one end of which is connected to said supporting means and the other end of which is connected to said heat insulated vessel.

In the apparatus mentioned above, the incident angle of the ultrasonic beam to the specimen can be adjusted precisely, and thus it is possible to obtain a ultrasonic image having higher resolving power.

Further, according to the sixth aspect of the invention, an ultrasonic microscope apparatus comprises:

a heat insulated vessel having an opening at the upper portion thereof for containing a cryogenic fluid serving as an ultrasonic propagating medium;

a sample rod having one end on which a specimen to be observed is supported, said sample rod being introduced into and withdrawn from said heat insulated vessel via said opening such that the specimen is immersed in the cryogenic fluid;

an acoustic lens arranged in said heat insulated vessel such that the acoustic lens is immersed in the cryogenic fluid for making an ultrasonic beam incident upon said specimen;

scanning means for driving said specimen and said acoustic lens in two dimensional directions relative to each other; and vapor pressure adjusting means for keeping the vapor pressure of said cryogenic fluid within said heat insulated vessel constant.

The cryogenic fluid which is contained in the vessel continues to vaporize in accordance with the heat inflow from outside the vessel. If the heat insulated vessel is closed up tightly, boiling of the cryogenic fluid can be stopped because the vapor pressure of the space which is in contact with the cryogenic fluid would be increased. On the other hand, if the heat insulated vessel is to be closed up tight for a long time, the vapor pressure of the space in the vessel would increase too much thereby causing many drawbacks as mentioned above (for example, deviation of the supporting member of the sample rod). Therefore, according to the sixth aspect of the invention, observation is conducted under such a condition that the vapor pressure of the space within the vessel is kept almost constant to the extent that the fluid does not boiled. As a result, it is possible to observe the specimen under the condition that the cryogenic fluid does not boil and the focal point of the acoustic lens can be adjusted precisely to the desired part of the specimen.

DETAILED DESCRIPTION OF THE PREFERRED EMBODIMENTS

Figure 1:
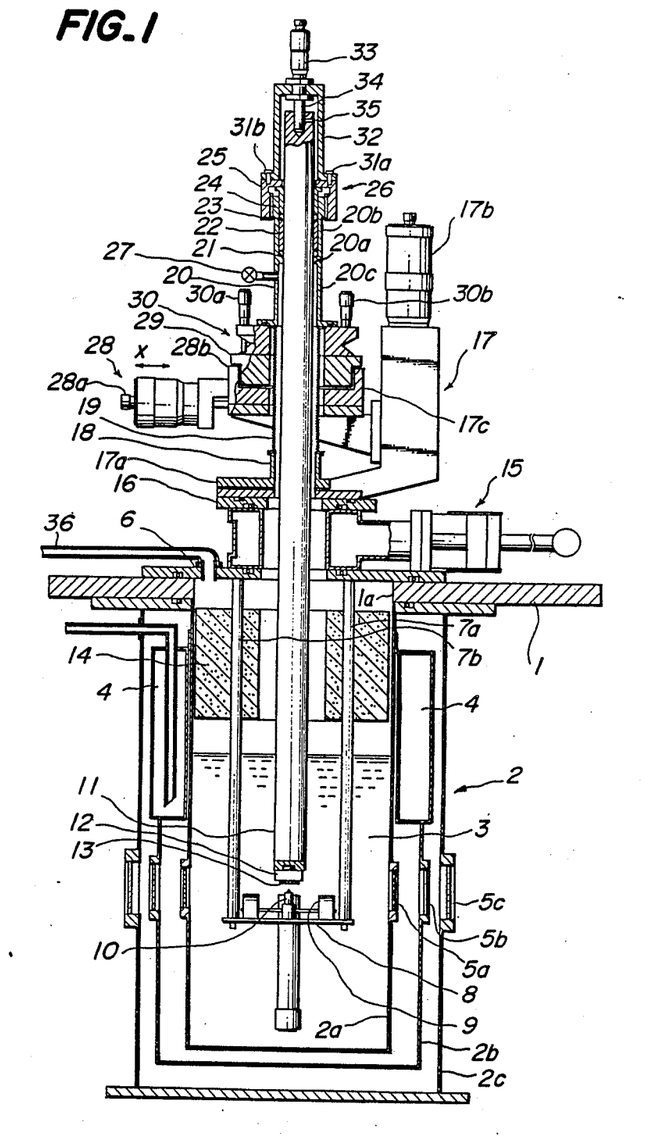
FIG. 1 is a schematic sectional view showing an embodiment of the ultrasonic microscope apparatus according to the present invention.

FIG. 1 is a schematical sectional view showing one embodiment of the ultrasonic microscope apparatus according to the invention.

A heat insulated vessel 2 is airtightly mounted to a vibration proof stand 1 and liquid nitrogen 3 is contained in said vessel 2 as an ultrasonic propagating medium. This heat insulated vessel 2 has an opening at the upper portion thereof and said vibration proof stand 1 also has an opening 1a corresponding to the opening of said vessel 2. The heat insulated vessel 2 has three vessel portions 2a, 2b and 2c forming a double vacuum layer, and a ring shaped tank 4 arranged at the upper portion of the middle vessel portion 2b. Liquid nitrogen is contained in the tank 4 in order to prevent the outside heat from increasing the temperature of the vessel 2. Windows 5a, 5b and 5c are arranged in the side walls of said vessel portions 2a, 2b and 2c, respectively of the heat insulated vessel 2 and thus the distance between an acoustic lens and a specimen arranged therein can be monitored from the external therethrough. A base flange 6 is closed up tightly on the vibration proof stand 1 via O-rings. This base flange 6 has an opening in the center thereof and four stays 7 are also mounted around the opening downwardly. (In order to make the drawing clear, only two stays 7a and 7b are illustrated in FIG. 1). A scanner stand 8 is mounted at the lower ends of the stays 7, x-y scanner 9 is mounted on the scanner stand 8, and an acoustic lens 10 is arranged on the x-y scanner 9. Therefore, the acoustic lens 10 may be driven in two-dimensional directions in the horizontal plane by the x-y scanner 9. A sample rod 11 which is extending to the z-direction upwardly is arranged above said acoustic lens 10, a specimen stand 12 is mounted to the lower end of the sample rod 11, and a specimen 13 to be observed is mounted on the specimen stand 12. An ultrasonic beam emitted from the acoustic lens 10 propagates in the liquid nitrogen 3 and arrives at the specimen 13, and thus the specimen 13 is scanned in two-dimensional directions by the ultrasonic beam. The reflected wave from the specimen 13 is collected by the acoustic lens 10 and converted to an electric signal by a piezo-electric transducer (not shown). Then the converted electric signal is processed to derive an image signal via a circulator and a signal processing circuit (not shown). The sample rod 11 is constituted by a hollow pipe made by stainless. Lead lines for the acoustic lens and x-y scanner are extended to the outside of the heat insulated vessel 2 through the side wall portion thereof or through a hole formed in the base flange 6 with a sealing device, and then connected to an external circuit. If the sample rod 11 is made by the material having the same thermal expansion coefficient as that of the material of the stays 7, it can be prevent to generate a deviation of the specimen 13 to the acoustic lens 10 in z-direction which is caused by the change of the level of the liquid nitrogen 3.

Around the opening of the heat insulated vessel 2, a ring shaped heat insulating member 14 is arranged in order to carry out heat insulating effect. A gate valve 15 is arranged on the base flange 6 via an O-ring, and when exchanging the specimen the heat insulated vessel 2 is closed up tightly by the valve 15. In the present embodiment, the gate valve 15 is formed by a slide valve having an opening. It is possible to adopt many sorts of valves for this purpose and therefore the detailed explanation thereof is omitted here. A flange 16 is mounted on the gate valve 15 via an O-ring and a base 17a for the z-direction adjusting device 17 is coaxially mounted on the flange 16 via O-ring. The z-direction adjusting device 17 is provided for adjusting the focal point by moving the sample rod 11 into the z-direction via a slide seal which is supporting the sample rod mentioned later. The z-direction adjusting device 17 comprises a base 17a secured to the flange 16, a micrometer 17b and a movable table 17c, and the movable table 17c is freely moved in the z-direction by rotating the adjusting knob of the micrometer via a connecting mechanism (not shown). Many kinds of adjusting devices can be adapted for this purpose, thus a detailed explanation is omitted here.

A sleeve 18 and a bellows 19 are coaxially mounted on the base 17a of the z-direction adjusting device 17. The bellows 19 functions as a member for closing up a hollow space formed on the vessel 2, said hollow space being transformable in the z-direction and also in x-y directions which are perpendicular to said z-direction.

Furthermore, a sleeve 20 for composing the slide seal and holding the sample rod 11 is mounted above the bellows 19. The sleeve 20 comprises a ring portion 20a which is formed at the center portion of the sleeve in the longitudinal direction and has a diameter a little larger than the outer diameter of the sample rod 11, and upper and lower sleeve portions 20b and 20c having a diameter larger than the outer diameter of the sample rod 11 and formed at the upper and lower portions of said ring portion 20a, respectively. A first O-ring 21, a first sleeve 22, a second O-ring 23 and a second sleeve 24 are successively mounted in the annular space formed between the upper sleeve 20b and the sample rod 11. Further, an end cap 25 is screwed onto the outer circumference of the upper sleeve portion 20b. The end portion of sample rod 11 is airtightly supported by binding the end cap 25 via the first and second O-rings 21 and 23. Therefore, these members mentioned above constitute a slide seal 26 which supports the sample rod 11.

The slide seal 26 has three kinds of operational modes in accordance with the extent to which the end cap 25 is bound. That is to say, the first mode is that the sample rod 11 can be moved relative to the slide seal so that the sample rod 11 moves independently because the end cap 25 is completely loosened. The second mode is that the sample rod 11 can be moved in the z-direction as keeping the space airtight because the end cap 25 is bound loosely. The third mode is that the slide seal 26 moves integrally with the sample rod 11 because the end cap 25 is bound tightly.

That is to say, an airtight space, which is transformable into x-, y- and z-directions, is formed around the sample rod 11 by the hollow members like the gate valve 15, the slide seal 26, the bellows 19, etc. Hereinafter, this space formed by these hollow members is called as top loading space.

Furthermore, a pumping line 27 is connected to the upper sleeve portion 20c of the sleeve 20, and the vacuum exhausting and the filling up a particular gas of the top loading space are conducted via the pumping line 27. On the other hand, on the movable table 17c, an x-direction adjusting device 28 and a y-direction adjusting device are arranged. These devices work to move the sample rod 11 parallelly in x- and y-directions, respectively. These two devices have the same structure and only x-direction adjusting device 28 is indicated in FIG. 1 in order to make the figure clear.

The x-direction adjusting device 28 comprises a micrometer 28a and an x-direction moving table 28b, and the x-direction moving table 28b is slidably moved in the x-direction by rotating the adjusting knob of the micrometer 28a via a spindle (not shown). Also, the y-direction adjusting device has a micrometer and a y-direction moving table 29. The micrometer for the y-direction adjusting device is arranged at the position which is separated from the micrometer 28a of the x-direction adjusting device by 90° viewed in the longitudinal direction of the sample rod 11. The y-direction moving table 29 is slidably movable on the x-direction moving table 28b and is moved in y-direction by rotating the adjusting knob of the micrometer of the y-direction adjusting device. The sample rod 11 can be parallelly airtightly moved in x- and y-directions by operating these x- and y-direction adjusting devices. According to the movements by means of these devices, the specimen mounted at the lower end of the sample rod 11 is parallelly moved in the x- and y-directions with respect to the acoustic lens 10. And it is possible to move the desired part of the specimen within the field of view of the acoustic lens 10. It is enough to make the movable range of these moving devices about 1 mm for this purpose. According to the construction mentioned above, it is possible to obtain a desired observation visual field while the top loading space and the space in the heat insulated vessel are kept airtight. An x-y inclination adjusting device 30 for use in spherical goniometer is arranged on the y-direction moving table 29 and the inclination of the sample rod 11 in x- and y-directions is adjusted thereby. The x-y inclination adjusting device comprises a concave spherical member and a convex spherical member engaged to each other and micrometers 30a and 30b. The inclinations in x- and y-directions of the sample rod is adjusted by operating the micrometers 30a and 30b. Since the inclination adjusting device for use in a spherical goniometer is already known, a detailed explanation is omitted here.

Furthermore, a bracket 32 is connected to the end cap 25 via two screws 31a and 31b. And, a differential micrometer 33 is mounted on the bracket 32, and a spindle 34 of the differential micrometer 33 is secured to the upper end portion of the sample rod 11 by means of a screw 35. This differential micrometer 33 functions as the z-direction ultrafine adjusting device for the sample rod 11. That is to say, the sample rod 11 is finely adjusted in z-direction by operating the differential micrometer 33 under the condition that the end cap 25 of the slide seal 26 is loosened to such an extent that airtightness is kept.

According to the construction mentioned above, it is possible to adjust the focus of the acoustic lens precisely, so that more clear ultrasonic images can be obtained.

Furthermore, in this embodiment, a tube 36 is connected to the base flange 6. As stated later, this tube 36 is arranged to keep the inner pressure of the space which contacts with the liquid nitrogen 3 contained in the heat insulated vessel 2 constant, and the nitrogen gas in this space is exhausted via the tube 36 when observing.

Next, the operation for exchanging specimens will be explained. After observing a specimen, the screw 35 is loosened to release the spindle 34 of the differential micrometer 33 from the sample rod 11, and thereafter the end cap 25 is loosened while the top loading space is kept airtight, and the sample rod 11 is pulled up to the extent that the stand 12 is lifted above the upper portion of the gate valve 15. Next, the gate valve 15 is closed to separate the space within the heat insulated vessel and the top loading space from each other in the airtight manner. Under this condition, the top loading space is exhausted via the pumping line 27 to make it vacuum and keep this condition until the sample rod 11 and the specimen 13 become to the room temperature. In this case, it is also possible to supply dried air or nitrogen gas having a high temperature or a room temperature to the loading space via the pumping line 27 in order to increase the temperature of the sample rod and specimen to the room temperature within a short time. After the temperature of the sample rod, etc. is increased to the room temperature, the slide seal 26 is opened and the sample rod and the specimen are taken off. According to such manner, the moisture of the outside can be prevented from adhering on the sample rod and the specimen. Next, the new specimen is mounted to the sample rod and the sample rod is inserted into the top loading space via the slide seal 26. Then the slide seal 26 is closed up, and the top loading space is exhausted to make a vacuum so that the sample rod and the new specimen is dried thereby. Next, the slide seal 26 is loosened with keeping the top loading space airtight and the gate valve 15 is opened, and the sample rod is inserted into the liquid nitrogen 3 as shown in FIG. 1. According to this structure, the air with moisture can be prevented from entering into the heat insulated vessel because when the sample rod is inserted into the vessel, the top loading space has been already exhausted, and therefore the drawback of moisture adherence can be prevented.

The specimen can be exactly positioned with respect to the acoustic lens because the position of the specimen can be observed via the windows 5a, 5b and 5c. Moreover, when observing the specimen, focusing is adjusted by operating the z-direction adjusting device 17 and the differential micrometer 33 which is connected to the upper end portion of the sample rod, and the inclination of the specimen is adjusted by operating the x-y inclination adjusting device 30, on the other hand, it is possible to select the desired part to be observed of the specimen by operating the x-direction adjusting device 28 and y-direction adjusting device.

Figure 2:
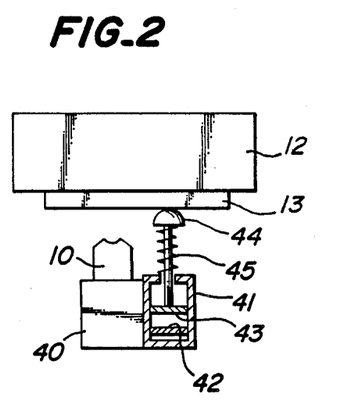
FIG. 2 is a schematic sectional view showing a collision preventing device for the acoustidc lens.

FIG. 2 is a schematic sectional view showing the device for preventing the specimen from coming into contact with the acoustic lens. When the specimen 13 is put on the observing position, there is a danger that the specimen will collided with the acoustic lens 10, thereby damaging the acoustic lens. Therefore, it is necessary to provide sufficient space between the specimen and the acoustic lens. For this purpose, a collision preventing device is provided beside an acoustic lens housing 40. The collision preventing device has a housing 41 wherein two parallel plate electrodes 42 and 43 are arranged to be faced to each other. The first plate electrode 42 is fixed at the inner wall of the housing 41 and the second plate electrode 43 is arranged to be movable. A pin 44 is secured to the backside of the second plate electrode 43 and a compressed spring 45 is put between the head of pin 44 and the housing 41, so that the second plate electrode 43 is biased to move toward the specimen. If the specimen 13 moves to the direction of the acoustic lens 10, the specimen 13 is first urged against the pin 44 and then the second plate electrode 43 moves closer to the first plate electrode 42. In this case, the distance between the specimen and the acoustic lens can be controlled by detecting the electrostatic capacity between the first and second electrodes 42 and 43, and thus preventing the specimen from colliding with the acoustic lens.

Figure 3:
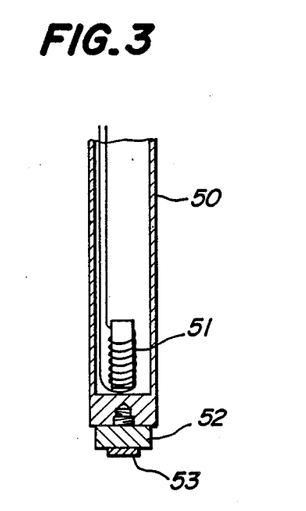
FIG. 3 is a schematic sectional view depicting a variation of the sample rod in which a heater is incorporated.

FIG. 3 is a schematic sectional view depicting a variation of the sample rod in which a heater is incorporated. It is necessary to place the specimen and the sample rod within the top loading space and to heat the specimen and the sample rod to the room temperature, when exchanging the specimen after observing. In the present embodiment, in order to make the heating time shorter, a heater 51 is incorporated within the end portion of the hollow-shaped sample rod 50. Therefore, the temperatures of the specimen stand 52 and the specimen 53 can be increased promptly up to the room temperature. As a result, the specimen exchanging operation can be conducted in a short time.

Figure 4:
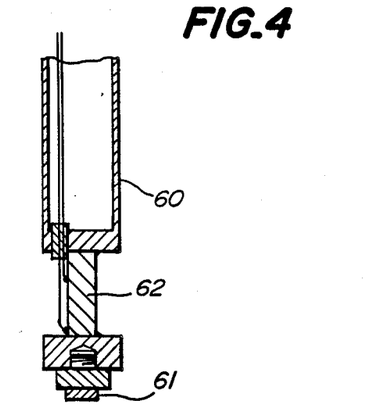
FIG. 4 is a schematic sectional view depicting a variation of the z-direction fine adjusting device.

FIG. 4 is a schematic sectional view showing a variation of the z-direction fine adjusting device. When observing the specimen, it is necessary to adjust the focus of the acoustic lens by precisely controlling the distance between the acoustic lens and the specimen. For this purpose, in this embodiment, there is provided a laminated type piezoelectric actuator element 62 between the end of the hollow-shaped sample rod 60 and the stand 61 for supporting the specimen, and the fine adjusting in z-direction is conducted thereby. Since this element has a piezoelectric effect and expands and contracts in correspondence with the applied voltage, it is possible to finely adjust the specimen in the z-direction by means of a simple operation. The lead wires of this element can be connected to the external circuit via the inner space of the sample rod 60. In such manner, since the sample rod has the inner space, it is possible to connect the lead wires of such an electric element to the external circuit with the simple structure.

Figure 5:
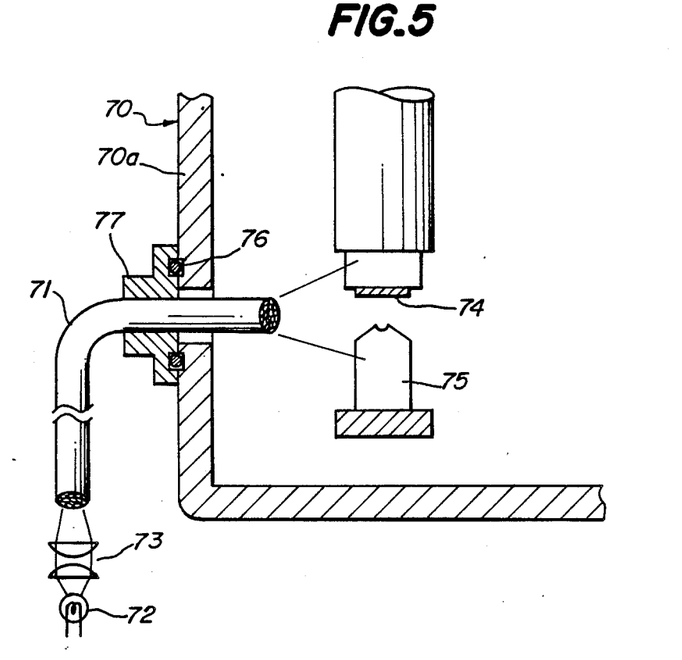
FIG. 5 is a schematic sectional view showing an illuminating device for illuminating the circumference of the acoustic lens.

FIG. 5 is a schematic sectional view showing an illuminating device for monitoring the acoustic lens and specimen. In this embodiment, the device illuminates the circumference of the acoustic lens and the specimen, so that the distance therebetween is recognized exactly from the outside the vessel. That is to say, it is necessary to adjust the distance roughly through the windows formed in the side walls of the heat insulated vessel. However, in order to keep the heat insulating effect of the vessel high, it is advantageous to make the windows small, and therefore, observation may be difficult due to the low illumination within the vessel. Thus, in this embodiment, there is provided an opening in the sidewall 70a of the heat insulated vessel 70, and an exit end of a light guide 71 is arranged inside of the heat insulated vessel 70 via the opening. At the incident side of the light guide 71, there are arranged a light source 72 and a lens system 73 to illuminate the circumference of the specimen 74 and the acoustic lens 75. The light guide 71 and the side wall 70a of the heat insulated vessel 70 are fixed tightly to each other by using an O-ring 76 and a resin seal 77. In such a manner, the illuminating device makes it possible to exactly recognize the distance between the specimen and the acoustic lens from outside the vessel without making the windows large, and thus the specimen can be easily set.

Figure 6A:
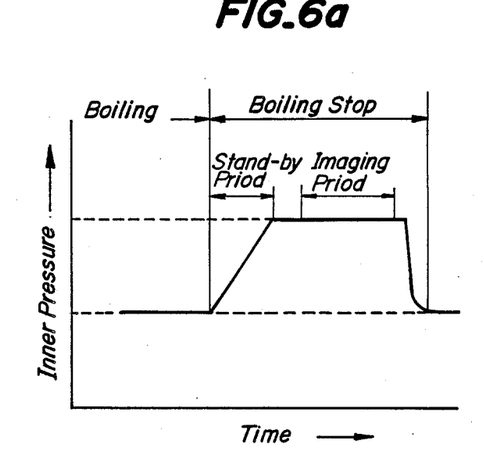
FIG. 6A is a graph for explaining the boiling stop device.
Figure 6B:
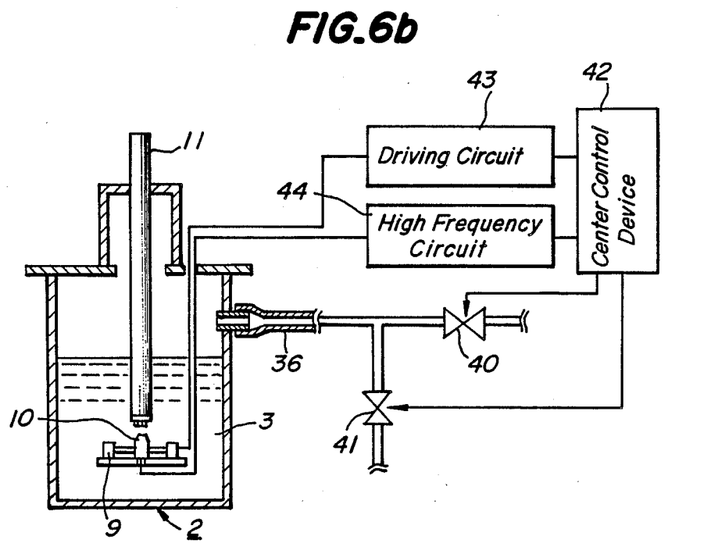
FIG. 6B is a schematic view showing the boiling stop device according to the invention.

Next, a boiling stop device for cryogenic fluid will be described. FIG. 6A is a graph for explaining the boiling stop function of the device, and FIG. 6B is a schematic view showing the structure of the boiling stop device. In order to keep the drawings clear, only the heat insulated vessel 2 and the circumferential portion thereof are illustrated schematically.

As shown in FIG. 6B, a tube 36, which is connected through the space in contact with the liquid nitrogen 3 in the heat insulated vessel 2, is divided into two lines, and an electromagnetic valve 40 is arranged in one of the lines and a needle valve 41 is put on the other. The electromagnetic valve 40 is opened and closed under the control of a central control device 42. The needle valve 41 is controlled to leak nitrogen gas when the pressure of the space in the vessel exceeds a given value under the control of the control device 42. Also, a scanner driving circuit 43 for the scanner 9 and a high frequency circuit 44 for generating a high frequency signal for the piezoelectric element secured to the acoustic lens 10 are connected to the central control device 42. After the sample rod 11 is set in the vessel 2, both the electromagnetic valve 40 and the needle valve 41 are closed by means of the control signals supplied from the central control device 42. Since the liquid nitrogen 3 is vaporized according to the heat inflow from the outside the vessel, the vapor pressure of nitrogen in the space being contacted with the liquid nitrogen 3 increases little by little, and thus the inner pressure of this space also increases gradually. On the other hand, the boiling point of the liquid nitrogen 3 increases as the vapor pressure of the space increases. Therefore, as shown in FIG. 6A, as the inner pressure of the space increases little by little, during boiling is stopped. After the lapse of a certain stand-by period from the point that the valves are closed, the needle valve 41 is switched to the slow leak state under controlling of the central control device 42. By the fact that the needle valve 41 is switched to the slow leak state, the inner pressure of the vessel 2 is kept constant to the extent that boiling is prevented. Since the vaporizing amount of the liquid nitrogen is substantially proportional to the temperature of the atmosphere surrounding the heat insulated vessel, the inner pressure of the vessel can be kept at the constant pressure $P_1$ under which the nitrogen is not boiled by controlling the stand-by period without detecting the pressure. In order to prevent boiling it is enough that the pressure $P_1$ is little higher than the normal pressure $P_0$. Therefore, in the present embodiment, the stand-by period and the pressure $P_1$ are decided on the basis of the room temperature and the amount of the liquid nitrogen remained in the vessel, after the lapse of the stand-by period the needle valve 41 is switched to the slow leak operation under the control of the central control device 42, the inner pressure of the vessel is kept at the pressure $P_1$ under which the nitrogen is not boiled, the central control device 42 supplies signals to the driving circuit 43 and the high frequency circuit 44, and then the imaging operation is conducted.

Thereafter, the needle valve 41 is closed and the electromagnetic valve 40 is released to bring the space into the normal pressure $P_0$. And, after that, the operation for exchanging the specimen is conducted.

Figure 7:
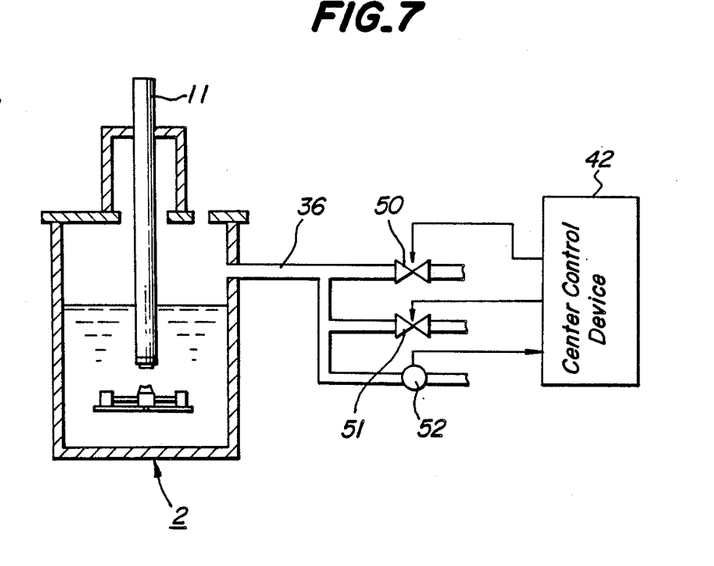
FIG. 7 is a schematic view showing a variation of the boiling stop device.

FIG. 7 is a schematic view showing the structure of another embodiment of the boiling stop device. In this embodiment, the tube 36 connected to the space within the vessel 2 is divided into three lines. An electromagnetic valve 50 is provided in the first line, a flow rate adjusting valve 51 is arranged in the second line, and a vapor pressure sensor 52 is inserted in the third line. In the embodiment illustrated in FIG. 6B, since the apparatus has no pressure detecting device, there is a danger that the pressure inside the vessel can not be kept exactly at the pressure $P_1$ at which liquid nitrogen will not boiled. Thus, in this embodiment, there is provided the pressure sensor 52 to detect the inner pressure of the space in contact with the liquid nitrogen, and the detected signal thereby is fed to the central control device 42. The central control device 42 controls the amount of the nitrogen gas released from the flow rate adjusting valve 51 based on the signal supplied from the pressure sensor 52 to keep the inner pressure of the space constant. After the imaging operation is finished, the electromagnetic valve 50 is opened to bring the inner pressure into the normal pressure $P_0$.

As explained above, according to the present invention, a top loading space is formed in addition to the observation space formed by the heat insulated vessel in which the cryogenic fluid is contained as an ultrasonic propagating medium such that these spaces can be selectively connected with each other. The sample rod, on the lower end of which the specimen to be observed is mounted, is introduced into and withdrawn from the heat insulated vessel through the top loading space as the vessel is kept airtight. Thus, preventing the moisture in the outside from entering into the vessel when the specimen is exchanged, so that the influence of the moisture can be completely avoided.

A part of members constituting the top loading space is made by bellows so that the top loading space becomes transformable, thus enabling the sample rod for supporting the specimen is parallelly movable in x- and y-directions while the top loading space is kept airtight. And the desired portion of the specimen can be placed within the field of view while keeping the vessel airtight.

Also, since the present invention provides a vapor pressure adjusting device by means of which the inner vapor pressure in the space in contact with the cryogenic fluid is kept at a constant pressure which is little higher than the normal pressure, the imaging operations can be carried out under such a condition where the cryogenic fluid is not boiled, and it is possible to remove the drawbacks caused by increasing the inner vapor pressure.

What is claimed is:

1. An ultrasonic microscope apparatus comprising:
   a heat insulated vessel having an opening at the upper portion thereof for containing a cryogenic fluid serving as an ultrasonic propagating medium;
   a sample rod having one end on which a specimen to be observed is supported, said sample rod being introduced into and withdrawn from said heat insulated vessel via said opening such that the specimen is immersed in the cryogenic fluid contained in the vessel;
   an acoustic lens arranged in said heat insulated vessel such that the acoustic lens is immersed in the cryogenic liquid, for making an ultrasonic beam incident upon said specimen, when the sample rod is inserted into said heat insulated vessel;
   scanning means for driving said acoustic lens in two-dimensional directions relative to the specimen;
   a sliding seal member adapted to selectively move between a first operational mode in which said seal member moves integrally with said sample rod, and a second operational mode in which the sample rod moves slidably relative to said sliding seal member; and
   a hollow airtight member arranged such that at least a part of said member is deformable, one end of which is airtightly connected to said sliding seal member and the other end of which is airtightly connected to said heat insulated vessel.

2. An ultrasonic microscope apparatus according to claim 1, wherein said cryogenic fluid is liquid nitrogen, liquid argon or liquid helium.

3. An ultrasonic microscope apparatus according to claim 1, wherein said sliding seal member comprises a first sleeve for slidably supporting the sample rod, a deformable sleeve having a portion arranged within a space formed between the sample rod and the first sleeve, and an end cap screwed to said first sleeve for selectively compressing said deformable sleeve such that the sliding seal member is driven into the first operational mode.

4. An ultrasonic microscope apparatus according to claim 1, wherein said hollow airtight member comprises bellows.

5. An ultrasonic microscope apparatus according to claim 1, wherein said heat insulated vessel comprises a window for monitoring the distance between said acoustic lens and said specimen outside from the vessel.

6. An ultrasonic microscope apparatus according to claim 5, further comprising a light guide for illuminating said acoustic lens and said specimen.

7. An ultrasonic microscope apparatus comprising:
   a heat insulated vessel having an opening at the upper portion thereof for containing a cryogenic fluid serving as an ultrasonic propagating medium;
   a sample rod having one end on which a specimen to be observed is supported, said sample rod being introduced into and withdrawn from said heat insulated vessel via said opening such that the specimen is immersed in said cryogenic fluid;
   an acoustic lens arranged in said heat insulated vessel such that the acoustic lens is immersed in the cryogenic fluid for making an ultrasonic beam incident upon said specimen;
   scanning means for driving said acoustic lens in two-dimensional directions relative to the specimen;
   a sliding seal member adapted to selectively move between a first operational mode in which it moves integrally with the sample rod and a second operational mode in which the sample rod moves slidably, relative to the sliding member;
   a hollow airtight member arranged such that at least a part of said member is deformable and having one end connected to said sliding seal member, said hollow airtight member forming together with said sliding seal member a top loading space;
   valve means arranged between the other end of said hollow airtight member and said opening of the heat insulated vessel for selectively communicating said top loading space and the heat insulated vessel with each other; and
   exhausting means for exhausting said top loading space.

8. An ultrasonic microscope apparatus according to claim 7, wherein said cryogenic fluid is liquid nitrogen, liquid argon or liquid helium.

9. An ultrasonic microscope apparatus according to claim 7, wherein said sliding seal member comprises a first sleeve for slidably supporting the sample rod, a deformable sleeve having a portion arranged within a space formed between the sample rod and the first sleeve, and an end cap screwed to said first sleeve for selectively compressing said deformable sleeve such that the sliding seal member is driven into the first operational mode.

10. An ultrasonic microscope apparatus according to claim 7, wherein said hollow airtight member comprises bellows.

11. An ultrasonic microscope apparatus according to claim 7, wherein said heat insulated vessel comprises a window for monitoring the distance between said acoustic lens and said specimen from outside the vessel.

12. An ultrasonic microscope apparatus according to claim 7, further comprising a light guide for illuminating said acoustic lens and said specimen.

13. An ultrasonic microscope apparatus according to claim 7, wherein said valve device is formed by a slide valve which separates said heat insulated vessel and the top loading space while they remain airtight.

14. An ultrasonic microscope apparatus according to claim 7, wherein said sample rod further comprises a heating means for heating said specimen.

15. An ultrasonic microscope apparatus comprising:
a heat insulated vessel having an opening at the upper portion thereof for containing a cryogenic fluid serving as an ultrasonic propagating medium;
a sample rod having one end on which a specimen to be observed is supported, said sample rod being introduced into and withdrawn from said heat insulated vessel via said opening such that the specimen is immersed in the cryogenic fluid contained in the vessel;
an acoustic lens arranged in said heat insulated vessel such that the acoustic lens is immersed in the cryogenic fluid for making an ultrasonic beam incident upon said specimen when the sample rod is inserted into said heat insulated vessel;
scanning means for driving said acoustic lens in two-dimensional directions relative to the specimen;
a supporting member for supporting said sample rod airtightly;
x-direction adjusting means for adjusting said sample rod in an x-direction which is perpendicular to the ultrasonic incident direction;
y-direction adjusting means for adjusting said sample rod in a y-direction which is perpendicular to the ultrasonic incident direction and said x-direction; and
a hollow airtight member arranged such that at least a part of said member is deformable in said x- and y-directions, one end of which is airtightly connected to said supporting member and the other one of which is airtightly connected to said heat insulated vessel.

16. An ultrasonic microscope apparatus according to claim 15, wherein said cryogenic fluid is liquid nitrogen, liquid argon or liquid helium.

17. An ultrasonic microscope apparatus according to claim 15, wherein said supporting member comprises a first sleeve for slidably supporting the sample rod, a deformable sleeve having a portion arranged within a space formed between the sample rod and the first sleeve, and an end cap screwed to said first sleeve for selectively compressing said deformable sleeve such that the supporting member is driven into a first operational mode.

18. An ultrasonic microscope apparatus according to claim 15, wherein said x-direction adjusting means comprises a micrometer and a movable table to move the sample rod parallelly in said x-direction.

19. An ultrasonic microscope apparatus according to claim 15, wherein said y-direction adjusting means comprises a micrometer and a movable table to move the sample rod parallelly in the y-direction.

20. An ultrasonic microscope apparatus according to claim 15, wherein said hollow airtight member comprises bellows.

21. An ultrasonic microscope apparatus according to claim 15, wherein said heat insulated vessel comprises a window for monitoring the distance between said acoustic lens and said specimen from outside the vessel.

22. An ultrasonic microscope apparatus according to claim 15, further comprising a light guide for illuminating said acoustic lens and said specimen.

23. An ultrasonic microscope apparatus comprising:
a heat insulated vessel having an opening at the upper portion thereof for containing a cryogenic fluid serving as an ultrasonic propagating medium;
a sample rod having one end on which a specimen to be observed is supported, said sample rod being introduced into and withdrawn from said heat insulated vessel via said opening such that the specimen is immersed in the cryogenic fluid;
an acoustic lens arranged in said heat insulated vessel such that the acoustic lens is immersed in the cryogenic fluid for making an ultrasonic beam incident upon said specimen;
scanning means for driving said acoustic lens in two dimensional directions relative to the specimen;
a supporting member for supporting said sample rod in an airtight manner;
z-direction ultrafine adjusting means for adjusting said sample rod in the ultrasonic incident direction; and
a hollow airtight member arranged such that at least a part of said member is deformable into the ultrasonic incident direction, one end of which is airtightly connected to said supporting member and the other end of which is airtightly connected to said heat insulated vessel.

24. An ultrasonic microscope apparatus according to claim 23, wherein said cryogenic fluid is liquid nitrogen, liquid argon or liquid helium.

25. An ultrasonic microscope apparatus according to claim 23, wherein said supporting member comprises a first sleeve for slidably supporting the sample rod, a deformable sleeve having a portion arranged within a space formed between the sample rod and the first sleeve, and an end cap screwed to said first sleeve for selectively compressing said deformable sleeve such that the supporting member is driven into a first operational mode.

26. An ultrasonic microscope apparatus according to claim 23, wherein said z-direction ultrafine adjusting means comprises a differential micrometer which is connected to the other end of said sample rod.

27. An ultrasonic microscope apparatus according to claim 23, wherein said hollow airtight member comprises bellows.

28. An ultrasonic microscope apparatus according to claim 23, wherein said heat insulated vessel comprises a window for monitoring the distance between said acoustic lens and said specimen from outside the vessel.

29. An ultrasonic microscope apparatus according to claim 23, further comprising a light guide for illuminating said acoustic lens and said specimen.

30. An ultrasonic microscope apparatus according to claim 23, wherein said apparatus further comprises means for preventing collision between said acoustic lens and said specimen.

31. An ultrasonic microscope apparatus according to claim 30, wherein said collision preventing means comprises a housing, first and second plate electrodes arranged parallel to each other, a pin secured to the back of one of said electrodes, and a compressed spring arranged between said pin and said housing.

32. An ultrasonic microscope apparatus according to claim 23, wherein said z-direction ultrafine adjusting means comprises a laminated piezoelectric actuator arranged between the one end of said sample rod and a stand for supporting said specimen.

33. An ultrasonic microscope apparatus comprising:
a heat insulated vessel having an opening at the upper portion thereof for containing a cryogenic fluid serving as an ultrasonic propagating medium;
a sample rod having one end on which a specimen to be observed is supported, said sample rod being introduced into and withdrawn from said heat insulated vessel via said opening such that the specimen is immersed in said cryogenic fluid;
an acoustic lens arranged in said heat insulated vessel such that the acoustic lens is immersed in the cryogenic fluid for making an ultrasonic beam incident upon said specimen;
scanning means for driving said acoustic lens in two-dimensional directions relative to said specimen;
supporting means for supporting said sample rod airtightly;
inclination adjusting means connected to said supporting means for adjusting the inclination of the sample rod in mutually orthogonal x- and y-directions which are perpendicular to an ultrasonic incident direction; and
a hollow airtight member arranged such that at least a part of said member is deformable in said x and y directions, one end of which is connected to said supporting means and the other end of which is connected to said heat insulated vessel.

34. An ultrasonic microscope apparatus according to claim 33, wherein said cryogenic fluid is liquid nitrogen, liquid argon or liquid helium.

35. An ultrasonic microscope apparatus according to claim 33, wherein said supporting means comprises a first sleeve for slidably supporting the sample rod, a deformable sleeve having a portion arranged within a space formed between the sample rod and the first sleeve, and an end cap screwed to said first sleeve for selectively compressing said deformable sleeve such that the supporting means is driven into a first operational mode.

36. An ultrasonic microscope apparatus according to claim 33, wherein said hollow airtight member comprises bellows.

37. An ultrasonic microscope apparatus according to claim 33, wherein said heat insulated vessel comprises a window for monitoring the distance between said acoustic lens and said specimen from outside the vessel.

38. An ultrasonic microscope apparatus according to claim 33, further comprising a light guide for illuminating said acoustic lens and said specimen.

39. An ultrasonic microscope apparatus according to claim 33, wherein said inclination adjusting means comprises a concave spherical member and a convex spherical member slidably engaged with each other, a first micrometer for adjusting the inclination in the x-direction and a second micrometer for adjusting the inclination in the y-direction.

40. An ultrasonic microscope apparatus comprising:
a heat insulated vessel having an opening at the upper portion thereof for containing a cryogenic fluid serving as an ultrasonic propagating medium;
a sample rod having one end of which a specimen to be observed is supported, said sample rod being introduced into and withdrawn from said heat insulated vessel via said opening such that the specimen is immersed in the cryogenic fluid;
an acoustic lens arranged in said heat insulated vessel such that the acoustic lens is immersed in the cryogenic fluid for making an ultrasonic beam incident upon said specimen;
scanning means for driving said specimen and said acoustic lens in two dimensional directions relative to each other; and
vapor pressure adjusting means for maintaining the vapor pressure of a space formed above the cryogenic fluid in said heat insulated vessel constant at a given value at which the cryogenic fluid contained in the vessel is not boiled.

41. An ultrasonic microscope apparatus according to claim 40, wherein said cryogenic fluid is liquid nitrogen, liquid argon or liquid helium.

42. An ultrasonic microscope apparatus according to claim 40, wherein further comprising a sliding seal member having a first sleeve for slidably supporting the sample rod, a deformable sleeve having a portion arranged within a space formed between the sample rod and the first sleeve, and an end cap screwed to said first sleeve for selectively compressing said deformable sleeve such that the sliding seal member is driven into a first operational mode.

43. An ultrasonic microscope apparatus according to claim 40, wherein said heat insulated vessel comprises a window for monitoring the distance between said acoustic lens and said specimen from outside the vessel.

44. An ultrasonic microscope apparatus according to claim 40, further comprising a light guide for illuminating said acoustic lens and said specimen.

45. An ultrasonic microscope apparatus according to claim 40, wherein a piezoelectric element secured to said acoustic lens is connected to a high frequency circuit and said scanning means comprising a scanner driving circuit both of which are controlled by a central control device.

46. An ultrasonic microscope apparatus according to claim 45, wherein said vapor pressure adjusting means comprises first and second tubes each being communicated with said heat insulated vessel, an electromagnetic valve provided in the first tube, and a needle valve provided in the second tube, said electromagnetic valve and said needle valve being controlled by said central control device in accordance with signals supplied from said high frequency circuit and said scanner driving circuit.

47. An ultrasonic microscope apparatus according to claim 45, wherein said vapor pressure adjusting means comprises first, second and third tubes each being communicated with said heat insulated vessel, an electromagnetic valve provided in the first tube, a flow rate adjusting valve provided in the second tube and a vapor pressure sensor provided in the third tube, said electromagnetic valve and said flow rate adjusting valve being controlled by said central control device in accordance with an output signal supplied from said vapor pressure sensor.

* * * * *

UNITED STATES PATENT AND TRADEMARK OFFICE
CERTIFICATE OF CORRECTION

PATENT NO. : 4,920,803
DATED : May 1, 1990
INVENTOR(S) : Karaki et al.

It is certified that error appears in the above-identified patent and that said Letters Patent is hereby corrected as shown below:

Title page:

After "[22] Filed: Aug. 24, 1988" insert:

--[30] Foreign Application Priority Data

Aug. 27, 1987 [JP]   Japan ........... 211,362/87
    Feb. 26, 1988 [JP]   Japan ........... 43,458/88--

Signed and Sealed this

Sixth Day of August, 1991

*Attest:*

HARRY F. MANBECK, JR.

*Attesting Officer*     *Commissioner of Patents and Trademarks*